(12) United States Patent
Han et al.

(10) Patent No.: US 11,871,787 B2
(45) Date of Patent: Jan. 16, 2024

(54) AEROSOL GENERATION METHOD AND APPARATUS

(71) Applicant: KT&G CORPORATION, Daejeon (KR)

(72) Inventors: Jung Ho Han, Daejeon (KR); Jang Uk Lee, Seoul (KR); Hun Il Lim, Seoul (KR); Jong Sub Lee, Seongnam-si (KR); Dae Nam Han, Daejeon (KR); Jin Young Yoon, Seoul (KR); Young Lea Kim, Seoul (KR); Ji Soo Jang, Seoul (KR); Wang Seop Lim, Anyang-si (KR); Moon Bong Lee, Seoul (KR); Soung Ho Ju, Daejeon (KR); Du Jin Park, Seoul (KR); Seong Won Yoon, Yongin-si (KR)

(73) Assignee: KT&G CORPORATION, Daejeon (KR)

( * ) Notice: Subject to any disclaimer, the term of this patent is extended or adjusted under 35 U.S.C. 154(b) by 337 days.

(21) Appl. No.: 16/608,511

(22) PCT Filed: Apr. 9, 2018

(86) PCT No.: PCT/KR2018/004115
§ 371 (c)(1),
(2) Date: Oct. 25, 2019

(87) PCT Pub. No.: WO2018/199504
PCT Pub. Date: Nov. 1, 2018

(65) Prior Publication Data
US 2021/0112868 A1    Apr. 22, 2021

(30) Foreign Application Priority Data

Apr. 28, 2017 (KR) .................. 10-2017-0055757
Jan. 25, 2018 (KR) .................. 10-2018-0009603

(51) Int. Cl.
*A24F 40/46* (2020.01)
*A24B 15/167* (2020.01)
(Continued)

(52) U.S. Cl.
CPC ............ *A24F 40/46* (2020.01); *A24B 15/167* (2016.11); *A24D 3/17* (2020.01); *A24F 7/04* (2013.01);
(Continued)

(58) Field of Classification Search
None
See application file for complete search history.

(56) References Cited

U.S. PATENT DOCUMENTS 8,459,271 B2    6/2013   Inagaki
8,517,032 B2    8/2013   Urtsev et al.
(Continued)

FOREIGN PATENT DOCUMENTS

CN    201719992 U    1/2011
CN    105163611 A    12/2015
(Continued)

OTHER PUBLICATIONS

International Search Report for PCT/KR2018/004115 dated Jul. 30, 2018 [PCT/ISA/210].
(Continued)

*Primary Examiner* — Kelly M Gambetta
*Assistant Examiner* — Katherine A Will
(74) *Attorney, Agent, or Firm* — Sughrue Mion, PLLC

(57) ABSTRACT

According to an exemplary embodiment, provided is an aerosol generation apparatus including: a liquid cartridge comprising a storage unit configured to store an aerosol-generating substrate which is liquid-type and an atomizer configured to generate aerosol by heating the aerosol-generating substrate; a mouth tip located at one end of the
(Continued)

aerosol generation apparatus and comprising a filter unit configured to adsorb at least one material included in the generated aerosol; and an aerosol heating unit configured to heat the generated aerosol when the generated aerosol is inhaled by a user through the mouth tip.

8 Claims, 3 Drawing Sheets

(51) Int. Cl.
    *A24F 40/10* (2020.01)
    *A24F 40/20* (2020.01)
    *A24F 40/30* (2020.01)
    *A24F 40/51* (2020.01)
    *A24D 3/17* (2020.01)
    *A24F 7/04* (2006.01)

(52) U.S. Cl.
    CPC .............. *A24F 40/10* (2020.01); *A24F 40/20* (2020.01); *A24F 40/30* (2020.01); *A24F 40/51* (2020.01)

(56) References Cited

U.S. PATENT DOCUMENTS

| | | |
|---|---|---|
| 10,136,673 B2 | 11/2018 | Mironov |
| 10,206,428 B2 | 2/2019 | Thorens et al. |
| 10,602,773 B2 * | 3/2020 | Biel ........................ A24F 40/40 |
| 10,881,137 B2 | 1/2021 | Suzuki et al. |
| 2011/0088707 A1 | 4/2011 | Hajaligol |
| 2014/0261486 A1 | 9/2014 | Potter et al. |
| 2016/0081395 A1 | 3/2016 | Thorens et al. |
| 2016/0324216 A1 | 11/2016 | Li et al. |
| 2017/0042243 A1 | 2/2017 | Plojoux et al. |
| 2018/0103685 A1 * | 4/2018 | Yener ...................... A24F 40/46 |
| 2019/0166916 A1 | 6/2019 | Robinson et al. |

FOREIGN PATENT DOCUMENTS

| | | |
|---|---|---|
| EP | 3085257 A1 | 10/2016 |
| EP | 3097802 A1 | 11/2016 |
| EP | 3082484 B1 | 10/2019 |
| JP | 2010-506594 A | 3/2010 |
| JP | 2011-518638 A | 6/2011 |
| JP | 2016-510994 A | 4/2016 |
| JP | 2017-511123 A | 4/2017 |
| KR | 10-2015-0127616 A | 11/2015 |
| KR | 10-2016-0008524 A | 1/2016 |
| KR | 10-2016-0098212 A | 8/2016 |
| KR | 10-2016-0140608 A | 12/2016 |
| KR | 10-2017-0008726 A | 1/2017 |
| WO | 2010/110226 A1 | 9/2010 |
| WO | 2016/159013 A1 | 10/2016 |

OTHER PUBLICATIONS

Office Action dated Jul. 12, 2021 in Chinese Application No. 201880024026.6.
Office Action dated Jun. 22, 2021 in Japanese Application No. 2019-555445.
Communication dated Jan. 5, 2021 from the Japanese Patent Office in Application No. 2019-555445.
Extended European Search Report dated Jan. 13, 2021 from the European Patent Office in Application No. 18791076.5.
Communication dated Jul. 7, 2020, from the Korean Intellectual Property Office in application No. 10-2018-0009603.

* cited by examiner

AEROSOL GENERATION METHOD AND APPARATUS

TECHNICAL FIELD

The present disclosure relates to aerosol generation methods and apparatuses.

BACKGROUND ART

Recently, the demand for alternative methods to overcome the shortcomings of general cigarettes has increased. For example, the demand for aerosol generation apparatuses that generate aerosol by heating a liquid aerosol generation material, not a cigarette, has increased. Accordingly, studies about a liquid heating-type aerosol generation apparatus are widely being performed.

General aerosol generation apparatuses may include a liquid cartridge and a mouthpiece, and allow a user to inhale aerosol generated from the liquid cartridge through the mouthpiece. A mouthpiece included in a general aerosol generation apparatus is made of a plastic material or a metal material. Accordingly, it may be difficult for a user to feel similar softness as ordinary cigarettes, from the mouthpiece of the aerosol generation apparatus. Furthermore, the mouthpiece formed of a plastic material or a metal material is designed to be used semi-permanently without replacement. Therefore, hygiene problems may occur when a user uses the aerosol generation apparatus for a long time, because the mouthpiece comes into contact with the mouth of the user.

Meanwhile, as the temperature of aerosol is lowered in a process of transferring the aerosol generated by the liquid cartridge of the aerosol generation apparatus to the user through the mouthpiece, the user may have difficulty feeling the warmth of the aerosol as in smoking an ordinary cigarette. Also, as the aerosol with a reduced temperature is liquefied again, droplets may be generated, which may cause the user to swallow liquid. In order for the liquid heating-type aerosol generation apparatus to provide an improved smoking experience to users, technology for solving the above-mentioned problems is needed.

DETAILED DESCRIPTION OF EXEMPLARY EMBODIMENTS

Technical Solution

Various exemplary embodiments provide aerosol generation methods and apparatuses. In detail, various exemplary embodiments provide aerosol generation apparatuses which may include a liquid cartridge including a storage unit for storing a liquid aerosol-generating substrate and an atomizer for generating aerosol by heating the aerosol-generating substrate, a mouth tip disposed at one end of the aerosol generation apparatus and including a filter unit for adsorbing at least one material included in the generated aerosol, and an aerosol heating unit for heating the generated aerosol when the generated aerosol is inhaled by a user through the mouth tip.

Advantageous Effects of Disclosure

The present disclosure may provide aerosol generation methods and apparatuses. In detail, an aerosol generation apparatus according to the present disclosure may provide a mouth tip disposed at one end of the aerosol generation apparatus and including a filter unit for adsorbing at least one material included in aerosol. As the mouth tip included in the aerosol generation apparatus according to the present disclosure is formed as a mouth tip portion of a general cigarette, a user may feel softness as in smoking a general cigarette from the mouth tip of the aerosol generation apparatus. Furthermore, as the mouth tip is detachable from the aerosol generation apparatus, even when a user uses the aerosol generation apparatus for a long time, hygiene problems may not occur by only replacing the mouth tip.

Furthermore, the aerosol generation apparatus according to the present disclosure may provide an aerosol heating unit for heating the generated aerosol when the generated aerosol is inhaled by a user through the mouth tip. Accordingly, as the aerosol generated by a liquid cartridge is reheated in a process of being transferred to a user through the mouth tip, the user may feel warmth of the aerosol as in smoking a general cigarette, and an occurrence of droplets or a liquid swallowing phenomenon due to back-liquefaction of the aerosol with a reduced temperature may be prevented.

BEST MODE

Figure 1:
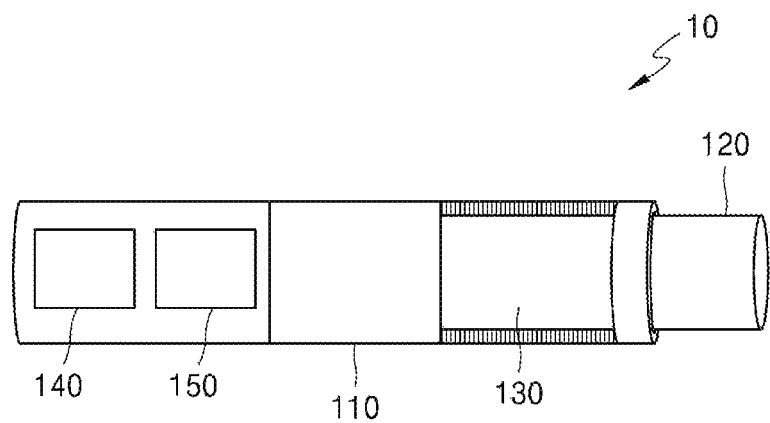
FIG. 1 illustrates the configuration of an aerosol generation apparatus according to an exemplary embodiment.

An aerosol generation apparatus includes a liquid cartridge including a storage unit for storing a liquid aerosol-generating substrate and an atomizer for generating aerosol by heating the aerosol-generating substrate, a mouth tip disposed at one end of the aerosol generation apparatus and including a filter unit for adsorbing at least one material included in the generated aerosol, and an aerosol heating unit for heating the generated aerosol when the generated aerosol is inhaled by a user through the mouth tip.

The aerosol heating unit may be located on a flow path connecting the liquid cartridge with the mouth tip.

Furthermore, the aerosol heating unit may include a separate heater or a heat generation material which is distinguished from the heater included in the atomizer.

In an exemplary embodiment, the aerosol heating unit may heat the generated aerosol to a temperature in a range of 20° C. to 40° C.

In an exemplary embodiment, the aerosol heating unit may heat at least part of the mouth tip.

In an exemplary embodiment, the mouth tip may include an aluminum foil surrounding at least part of the mouth tip.

Furthermore, the mouth tip may be detachable from the aerosol generation apparatus.

Meanwhile, the aerosol generation apparatus may further include a sensor part including at least one of a negative pressure sensor, a proximity sensor, and an infrared sensor, and an electronic circuit configured to supply power to at least one of the atomizer and the aerosol heating unit according to a signal detected by the sensor part.

The aerosol-generating substrate may include at least one of an aerosol generation material, nicotine, moisture, and a flavoring material, and the aerosol generation material may include at least one of propylene glycol (PG) and glycerin. Furthermore, the aerosol-generating substrate may include a gel or solid content type material.

Meanwhile, the filter unit may include at least one of an acetate tow filter, a dual filter, a capsule filter, a tube filter, a recess filter, a cavity filter, and a TJNS filter.

Furthermore, the aerosol generation apparatus may further include a battery configured to supply power used to operate the aerosol generation apparatus; and an electronic circuit configured to control an operation of the aerosol generation apparatus.

MODE OF DISCLOSURE

Reference will now be made in detail to exemplary embodiments, which are illustrated in the accompanying drawings. However, the inventive concept is not limited to the embodiments illustrated hereinafter, and the exemplary embodiments herein are rather introduced to provide easy and complete understanding of the scope and spirit of the invention.

Terms such as "include" or "comprise" may not be construed to necessarily include any and all constituent elements or steps described in the specification, but may be construed to exclude some of the constituent elements or steps or further include additional constituent elements or steps.

Furthermore, terms such as "first" and "second" are used herein merely to describe a variety of constituent elements, but the constituent elements are not limited by the terms. Such terms are used only for the purpose of distinguishing one constituent element from another constituent element.

The terms used in the present disclosure are those selected from currently widely used general terms in consideration of functions in the present disclosure, but the terms may vary according to an engineer's intension, precedents, or advent of new technology. In addition, in certain cases, a term which is not commonly used may be selected. In such a case, the meaning of the term will be described in detail at the corresponding part in the description of the present disclosure. Therefore, the terms used in the various exemplary embodiments of the present disclosure should be defined based on the meanings of the terms and the descriptions provided herein.

In the entire specification, an "aerosol generation apparatus" may include an apparatus that generates aerosol by using an aerosol generation material to generate aerosol that can be inhaled directly to the lungs of a user through the mouth of the user.

In the entire specification, a "puff" may signify inhalation of a user, and the inhalation may mean a situation in which a certain material is drawn into the oral cavity, the nasal cavity, or the lungs of the user through the mouth or the nose of the user.

The exemplary embodiments relate to aerosol generation methods and apparatuses, and detailed descriptions on the matters that are well known to a person skilled in the art to which the following exemplary embodiments belong are omitted.

FIG. 1 illustrates the configuration of an aerosol generation apparatus according to an exemplary embodiment.

Referring to FIG. 1, an aerosol generation apparatus 10 may include a liquid cartridge 110, a mouth tip 120, an aerosol heating unit 130, a battery 140, and an electronic circuit 150. Meanwhile, the aerosol generation apparatus 10 illustrated in FIG. 1 includes only elements related to the present exemplary embodiment. Accordingly, a person skilled in the art would understand that other general use elements may be further included in the aerosol generation apparatus 10 in addition to the elements illustrated in FIG. 1.

The liquid cartridge 110 may include a storage unit (not shown) for storing an aerosol-generating substrate which is liquid-type and an atomizer (not shown) for generating aerosol by heating the aerosol-generating substrate. The storage unit may be provided in a form in which at least part of an outer surface thereof is sealed to store the aerosol-generating substrate which is liquid-type. Furthermore, the storage unit may include a capillary wick. The capillary wick may transfer the aerosol-generating substrate stored in the storage unit to the atomizer by using surface tension of liquid.

The atomizer may include a heater for generating aerosol by heating the aerosol-generating substrate. The heater may be in the form of a mesh or a coil, but the present disclosure is not limited thereto. The heater may include any form capable of heating the aerosol-generating substrate stored in the storage unit without limitation. The heater may include an electrically resistive heater. For example, a heating element may include an electrically conductive track, and the heating element may be heated as current flows in the electrically conductive track. However, this is a mere example, and the present disclosure is not limited thereto.

Meanwhile, the atomizer may include, instead of the heater, a module for generating aerosol without heating the liquid aerosol-generating substrate. For example, the atomizer may include a module for guiding the aerosol-generating substrate which is liquid-type to be aerosolized along a flow path through diffusion or evaporation.

Furthermore, the atomizer may include both the heater for generating aerosol by heating the aerosol-generating substrate which is liquid-type and the module for generating aerosol without heating the aerosol-generating substrate which is liquid-type.

The aerosol-generating substrate may include at least one of an aerosol generation material, nicotine, moisture, and a flavoring material. Furthermore, the aerosol-generating substrate may include various additive materials such as cinnamon or capsaicin. The aerosol-generating substrate may include not only a liquid material having a great fluidity, but also a gel or solid content type material.

The aerosol generation material may mean a material that may generate aerosol, and may mean aerosol forming properties. The aerosol generation material may include a volatile composition. For example, the aerosol generation material may include at least one of propylene glycol (PG) and glycerin. Furthermore, the aerosol generation material may further include at least one of ethylene glycol, dipropylene glycol, diethylene glycol, triethylene glycol, tetraethylene glycol, and oleyl alcohol.

Meanwhile, the nicotine included in the aerosol-generating substrate may include at least one of leaf tobacco extract, specific components extracted from leaf tobacco extract, and nicotine derivatives. The leaf tobacco extract may optionally include some of nicotine and other components extracted from the leaf tobacco. The nicotine derivatives may be selected by a method of chemically classifying specific nicotine among nicotine groups, and may be given a new function by a method of binding a functional group to nicotine molecules. Furthermore, the nicotine derivatives may correspond to nicotine salt produced by binding anions to nicotine cations.

The mouth tip 120 may include a filter unit (not shown) disposed at one end of the aerosol generation apparatus 10 and adsorbing at least one material included in the aerosol generated by the liquid cartridge 110. The mouth tip 120 may be identical to a mouth tip part of a general cigarette. Accordingly, the mouth tip 120 may give a user a sense of softness similar to the general cigarette. Furthermore, the filter unit included in the mouth tip 120 may prevent a phenomenon in which the liquid in the storage unit of the liquid cartridge 110 flows into the mouth of a user.

The filter unit included in the mouth tip 120 may include at least one of an acetate tow filter, a dual filter, a capsule filter, a tube filter, a recess filter, a cavity filter, and a TJNS filter. For example, the filter unit included in the mouth tip 120 may include one of an acetate tow filter, a dual filter, a capsule filter, a tube filter, a recess filter, a cavity filter, and a TJNS filter. Otherwise, the filter unit included in the mouth tip 120 may include a combination of two or more of an acetate tow filter, a dual filter, a capsule filter, a tube filter, a recess filter, a cavity filter, and a TJNS filter.

The acetate tow filter may signify a filter in which cellulose acetate is processed in a tow form. The dual filter may signify a filter in which a carbon filling material that adsorbs at least one material is bonded to the acetate tow filter. The carbon filling material may include at least one of carbon, active carbon, and carbonaceous polymer. For example, the carbon filling material may include active carbon including at least one of coconut-based active carbon, nut shell, drupe, charcoal, lignite, and organic polymer, but the present disclosure is not limited thereto. The carbon filling material may include an appropriate material that may adsorb at least one material.

The capsule filter may signify a filter in which capsules are included in the acetate tow filter. The capsule may include a flavoring material or a tobacco material. However, the material included in a capsule is not limited to the above-described example.

Meanwhile, the tube filter may signify a filter having a tube shape, and the recess filter may signify a filter including a cavity or a recess portion at an end portion thereof. The cavity filter may signify a filter having a cavity in the middle part thereof. A flavoring material, carbon, or water may be included in the cavity of the cavity filter. The TJNS filter may signify a filter that is manufactured by adding a flavoring component in a process of manufacturing the acetate tow filter.

The mouth tip 120 may have a cylindrical shape and may include a cavity. However, the shape of the mouth tip 120 is not limited to the above-described example and may have a polygonal section. Meanwhile, the mouth tip 120 may be detachable from the aerosol generation apparatus 10. Accordingly, the mouth tip 120 may be replaced by being separated from the aerosol generation apparatus 10. A case of the mouth tip 120 being detachable from the aerosol generation apparatus 10 is described below in detail with reference to FIG. 2.

Figure 2:
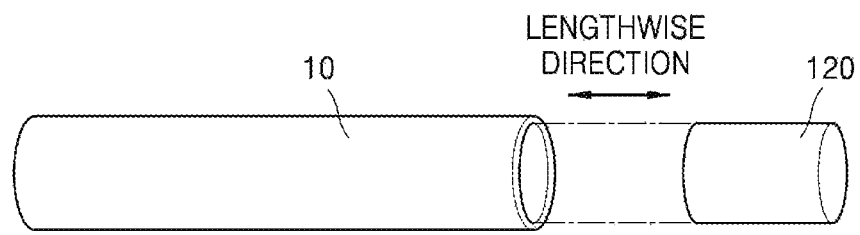
FIG. 2 illustrates an example of a mouth tip which is detachable from an aerosol generation apparatus according to an exemplary embodiment.

FIG. 2 illustrates an example of a mouth tip detachable from an aerosol generation apparatus according to an exemplary embodiment.

Referring to FIG. 2, the mouth tip 120 may be detachable from the aerosol generation apparatus 10 in a lengthwise direction. The mouth tip 120 may be replaced by being separated from the aerosol generation apparatus 10. The mouth tip 120, which is a portion contacting the mouth of a user, needs to be periodically replaced. Unlike a mouthpiece included in a conventional aerosol generation apparatus, the mouth tip 120 included in the aerosol generation apparatus 10 according to the present disclosure is replaceable. As such, even when a user uses the aerosol generation apparatus 10 for a long time, no hygiene problem is generated.

The mouth tip 120, when inserted into the aerosol generation apparatus 10, may be fixed by a fixing unit (not shown) provided in the aerosol generation apparatus 10. The fixing unit for fixing the mouth tip 120 to the aerosol generation apparatus 10 is described below in detail with reference to FIG. 3.

Figure 3:
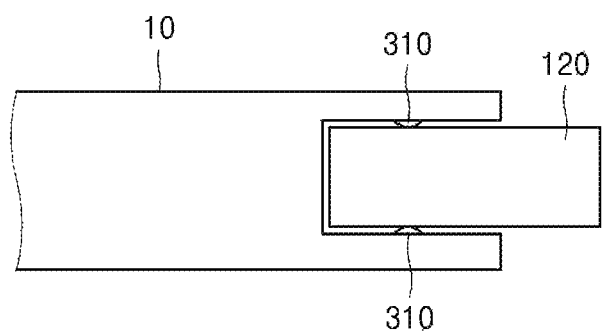
FIG. 3 illustrates an example of a fixing unit for fixing the mouth tip to an aerosol generation apparatus according to an exemplary embodiment.

FIG. 3 illustrates an example of a fixing unit for fixing the mouth tip to an aerosol generation apparatus according to an exemplary embodiment.

Referring to FIG. 3, the aerosol generation apparatus 10 may include at least one fixing unit 310 for fixing the mouth tip 120 when the mouth tip 120 is inserted into the aerosol generation apparatus 10. The at least one fixing unit 310 may be provided in the form of a spring and may apply a pressure to the mouth tip 120 to fix the mouth tip 120. However, this is a mere example, and the at least one fixing unit 310 may have another appropriate form to fix the mouth tip 120 and is not limited to the above example.

Referring back to FIG. 1, the aerosol heating unit 130 may heat the aerosol generated by the liquid cartridge 110. The user may inhale the aerosol heated by the aerosol heating unit 130. The aerosol heating unit 130 may be located on a flow path connecting the liquid cartridge 110 with the mouth tip 120. As the aerosol heating unit 130 heats the aerosol passing through the flow path, the user may feel warmth of the aerosol as in smoking a general cigarette. Furthermore, an occurrence of droplets or a liquid swallowing phenomenon occurring as the aerosol having a temperature that is reduced while passing through the flow path is liquefied back may be prevented.

The aerosol heating unit 130 may include a separate heater or a heat generation material which is distinguished from the heater included in the atomizer. For example, the aerosol heating unit 130 may include a heater for heating the aerosol, and may include a heat generation material that generates heat as the aerosol passes therethrough. However, the present disclosure is not limited thereto.

Meanwhile, the heater included in the aerosol heating unit 130 may be in the form of a cylinder. Accordingly, the heater included in the aerosol heating unit 130 may be configured to heat the aerosol that passes through an empty space in the heater. However, the present disclosure is not limited thereto, and the heater included in the aerosol heating unit 130 may be formed in a certain form suitable for heating the aerosol.

For example, the aerosol heating unit 130 may heat the aerosol generated by the liquid cartridge 110 to a temperature in a range of 20° C. to 40° C. Alternatively, the aerosol heating unit 130 may heat the aerosol generated by the liquid cartridge 110 in a range of about 50° C. However, the temperature to which the aerosol is heated is not limited to the above-described temperature. The aerosol heating unit 130 may heat the aerosol to an appropriate temperature so as to provide the user with the warmth of the aerosol as in smoking a general cigarette. Furthermore, the aerosol heating unit 130 may heat the aerosol to an appropriate temperature to prevent the occurrence of droplets or liquid swallowing phenomenon occurring as the aerosol generated by the liquid cartridge 110 is liquefied back on the flow path that passes through the mouth tip 120.

Meanwhile, the aerosol heating unit 130 may heat at least part of the mouth tip 120. As the aerosol heating unit 130 heats the at least part of the mouth tip 120, the user with the mouth tip 120 in the mouth may feel warmth. Accordingly, not only the warmth through the aerosol, but also the warmth from the contact with the mouth tip 120 may be provided to the user. Furthermore, smoking experience as in the smoking a general cigarette may be provided to the user.

The at least part of the mouth tip 120 may be heated by the heater or heat generation material included in the aerosol heating unit 130. However, this is a mere example, and the at least part of the mouth tip 120 may be heated by a heating element included in the mouth tip 120. Meanwhile, the aerosol heating unit 130 may heat the mouth tip 120 within an appropriate temperature range not affecting the properties of the mouth tip 120. For example, the aerosol heating unit 130 may heat the mouth tip 120 to a temperature in a range of 20° C. to 40° C. However, the present disclosure is not limited to the above-described temperature.

The mouth tip 120 may include an aluminum foil surrounding the at least part of the mouth tip 120. Accordingly, when the at least part of the mouth tip 120 is heated by the aerosol heating unit 130, heat conductivity from the aerosol heating unit 130 may be increased. The aluminum foil surrounding the at least part of the mouth tip 120 is described below in detail with reference to FIG. 4.

Figure 4:
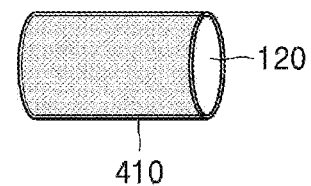
FIG. 4 is a perspective view showing an example of an aluminum foil surrounding at least part of the mouth tip according to an exemplary embodiment.

FIG. 4 is a perspective view showing an example of an aluminum foil surrounding at least part of the mouth tip according to an exemplary embodiment.

Referring to FIG. 4, an example of an aluminum foil 410 surrounding the at least part of the mouth tip 120 is illustrated. As the aluminum foil 410 is a thin film manufactured of an aluminum material having high heat conductivity, conductivity of the heat transferred to the mouth tip 120 may be increased by the aluminum foil 410. The aluminum foil 410 may surround the entire outer surface of the mouth tip 120 as illustrated in FIG. 4. However, the present disclosure is not limited to the example illustrated in FIG. 4, and the aluminum foil 410 may surround the at least part of the mouth tip 120 in an appropriate form. Furthermore, the aluminum foil 410 may be located inside the mouth tip 120. For example, when the mouth tip 120 has a cavity shape, the aluminum foil 410 may be located to surround at least part of an inner surface of the mouth tip 120.

Referring to back to FIG. 1, the battery 140 may supply power used to operate the aerosol generation apparatus 10. For example, the battery 140 may supply power to heat the heater included in the atomizer of the liquid cartridge 110 and a heater included in an aerosol heating unit 10, and may supply power to operate the electronic circuit 150. Furthermore, the battery 140 may supply power to operate a display, a sensor, or a motor which are installed in the aerosol generation apparatus 10.

The battery 140 may include a lithium iron phosphate (LiFePO$_4$) battery, but not limited to the above-described example. For example, the battery 140 may include a lithium cobalt oxide (LiCoO$_2$) battery or a lithium titanate battery.

The electronic circuit 150 may control the overall operation of the aerosol generation apparatus 10. For example, an electronic circuit 150 may control the operations of the liquid cartridge 110, the aerosol heating unit 130, and the battery 140. Also, the electronic circuit 150 may control the operations of other elements included in the aerosol generation apparatus 10. The electronic circuit 150 may control the power supplied by the battery 140, the temperature of the heater included in the atomizer of the liquid cartridge 110 and the temperature of the heater included in the aerosol heating unit 10. The electronic circuit 150 may check the state of each element of the aerosol generation apparatus 10 to determine whether the aerosol generation apparatus 10 is in an operable state.

The electronic circuit 150 may include at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware. For example, the processor may include an MCU, but the present disclosure is not limited thereto.

In detail, the electronic circuit 150 may control the operations of the heater included in the atomizer of the liquid cartridge 110 and the heater included in the aerosol heating unit 10. The electronic circuit 150 may control the amount and time of power supplied to the heater included in the atomizer of the liquid cartridge 110 and the heater included in the aerosol heating unit 10 so that the heater included in the atomizer of the liquid cartridge 110 and the heater included in the aerosol heating unit 10 may be heated to a certain temperature or maintained at an appropriate temperature.

Furthermore, the electronic circuit 150 may check the state of the battery 140, for example, the remaining amount of the battery 140 and generate a notification signal when necessary. Furthermore, the electronic circuit 150 may check the existence of a user's puff and the strength of a puff, and count the number of puffs. Furthermore, the electronic circuit 150 may continuously check the duration of the operation of the aerosol generation apparatus 10.

Meanwhile, the aerosol generation apparatus 10 may further include an input apparatus (not shown) for receiving a user input. The input apparatus may be implemented by a switch or a button, but the present disclosure is not limited thereto. For example, the input apparatus may be implemented by a touch screen. The electronic circuit 150 may control the aerosol generation apparatus 10 to generate aerosol as the user operates a switch or a button.

Furthermore, the aerosol generation apparatus 10 may further include a sensor part (not shown) including a negative pressure sensor, a proximity sensor, and an infrared sensor. However, an example of a sensor included in the aerosol generation apparatus 10 is not limited to the above-described sensor types. The sensor part may detect when the user performs a puff motion or contacts the aerosol generation apparatus 10. The electronic circuit 150 may supply power to at least one of the atomizer included in the liquid cartridge 110 and the aerosol heating unit 130 according to a signal detected by the sensor part. Accordingly, the aerosol generation apparatus 10 may generate aerosol by detecting that the user performs a puff motion or contacts the aerosol generation apparatus 10, without having a separate input apparatus.

The aerosol generation apparatus 10 may further include memory (not shown). The memory is hardware for storing various pieces of data processed in the aerosol generation apparatus 10. For example, the memory may store data that is processed and is to be processed in the aerosol generation apparatus 10. Furthermore, the memory may store applications or drivers driven by the aerosol generation apparatus 10.

The memory may include random access memory (RAM) such as dynamic random access memory (DRAM) or static random access memory (SRAM), read-only memory (ROM), electrically erasable programmable read-only memory (EEPROM), CD-ROM, Blueray, or other optical disk storage, hard disk drive (HDD), solid state drive (SSD), or flash memory, and furthermore, other external storage device to be accessed by the aerosol generation apparatus 10.

A detailed method by which the aerosol generation apparatus 10 is operated is described below in detail with reference to FIG. 5.

Figure 5:
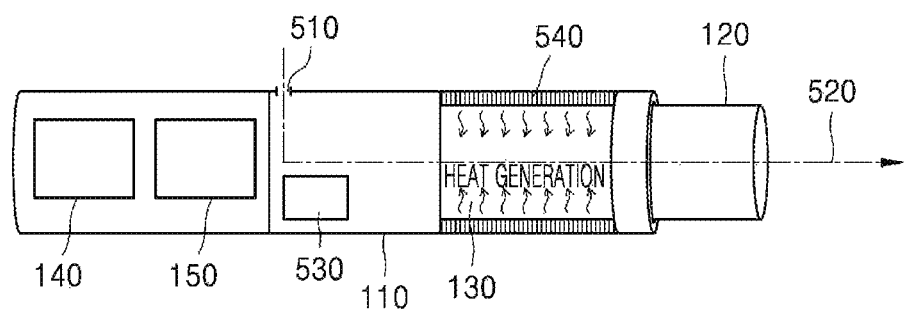
FIG. 5 illustrates an example of an operation of an aerosol generation apparatus according to an exemplary embodiment.

FIG. 5 illustrates an example of an operation of an aerosol generation apparatus according to an exemplary embodiment.

Referring to FIG. 5, the aerosol generation apparatus 10 may include at least one air inlet 510. The air introduced from the air inlet 510 to the inside of the aerosol generation apparatus 10 may pass through a flow path 520 connecting the liquid cartridge 110 and the mouth tip 120. Although FIG. 5 illustrates that the air inlet 510 is located at a side surface of the liquid cartridge 110, the present disclosure is not limited thereto. The air inlet 510 may be located at an appropriate portion of the aerosol generation apparatus 10. For example, the air inlet 510 may be located in at least a region of an outer surface of a housing including the battery 140 and a controller 150.

Meanwhile, the aerosol-generating substrate stored in the storage unit is heated by a first heater 530 included in the atomizer of the liquid cartridge 110, and thus aerosol may be generated. The generated aerosol may pass through the flow path 520 with the air introduced to the inside of the aerosol generation apparatus 10 from the air inlet 510.

Meanwhile, as the temperature of aerosol is reduced while the generated aerosol moves along the flow path 520, the user may not feel the warmth of the aerosol as in smoking a general cigarette. Also, as the aerosol having a reduced temperature is liquefied back, droplets may be generated and the user may swallow liquid.

To prevent the above problems, a second heater 540 included the aerosol heating unit 130 located on flow path 520 may reheat the aerosol on the flow path 520. As the generated aerosol is reheated, the user may feel the warmth of the aerosol as in smoking a general cigarette, and the occurrence of droplets or liquid swallowing phenomenon due to back-liquefaction of the aerosol having a reduced temperature may be prevented.

Furthermore, the second heater 540 included in the aerosol heating unit 130 may heat the at least part of the mouth tip 120. As the second heater 540 heats the at least part of the mouth tip 120, the user with the mouth tip 120 in the mouth may feel warmth. Accordingly, not only the warmth through the aerosol, but also the warmth felt from the contact with the mouth tip 120 may be provided to the user. Furthermore, smoking experience as in smoking a general cigarette may be provided to the user.

While this disclosure has been particularly shown and described with reference to exemplary embodiments thereof, it will be understood by those of ordinary skill in the art that various changes in form and details may be made therein without departing from the spirit and scope of the disclosure as defined by the appended claims. The exemplary embodiments should be considered in descriptive sense only and not for purposes of limitation. Therefore, the scope of the disclosure is defined not by the detailed description of the disclosure but by the appended claims, and all differences within the scope will be construed as being included in the present disclosure.

What is claimed is:

1. An aerosol generation apparatus comprising:
   a liquid cartridge comprising a storage unit configured to store an aerosol-generating substrate of a liquid-type and an atomizer configured to generate aerosol by heating the aerosol-generating substrate;
   a mouth tip located at one end of the aerosol generation apparatus and comprising a filter unit configured to adsorb at least one material included in the generated aerosol; and
   an aerosol heating unit configured to heat the generated aerosol when the generated aerosol is inhaled by a user through the mouth tip,
   wherein the aerosol is heated by the aerosol heating unit before reaching the mouth tip,
   wherein the mouth tip is detachable from the aerosol generation apparatus including the aerosol heating unit,
   wherein at least part of the mouth tip is surrounded by the aerosol heating unit when inserted into the aerosol generation apparatus such that the mouth tip is heated by the aerosol heating unit, and
   wherein at least part of the mouth tip is surrounded by an aluminum foil which is configured to transfer heat from the aerosol heating unit to the mouth tip.

2. The aerosol generation apparatus of claim 1, wherein the aerosol heating unit comprises a separate heater or a heat generation material, which is distinct from a heater included in the atomizer.

3. The aerosol generation apparatus of claim 1, wherein the aerosol heating unit is further configured to heat the generated aerosol to a temperature in a range of 20° C. to 40° C.

4. The aerosol generation apparatus of claim 1, further comprising:
   a sensor part comprising at least one of a negative pressure sensor, a proximity sensor, and an infrared sensor; and
   an electronic circuit configured to supply power to at least one of the atomizer and the aerosol heating unit according to a signal detected by the sensor part.

5. The aerosol generation apparatus of claim 1, wherein the aerosol-generating substrate comprises at least one of an aerosol generation material, nicotine, moisture, and a flavoring material.

6. The aerosol generation apparatus of claim 5, wherein the aerosol generation material comprises at least one of propylene glycol (PG) and glycerin.

7. The aerosol generation apparatus of claim 1, wherein the aerosol-generating substrate comprises a gel type material or a solid content type material.

8. The aerosol generation apparatus of claim 1, further comprising:
   a battery configured to supply power for operating the aerosol generation apparatus; and
   an electronic circuit configured to control an operation of the aerosol generation apparatus,
   wherein the filter unit comprises at least one of an acetate tow filter, a dual filter, a capsule filter, a tube filter, a recess filter, a cavity filter, and a transfer jet nozzle system (TJNS) filter.

* * * * *